(12) United States Patent
Kim et al.

(10) Patent No.: US 10,828,253 B2
(45) Date of Patent: Nov. 10, 2020

(54) COMPOSITION FOR INJECTION

(71) Applicant: HK INNO.N CORPORATION, Seoul (KR)

(72) Inventors: Hyo Jin Kim, Gyeonggi-do (KR); Sung Jun Kim, Gyeonggi-do (KR); Min Kyoung Lee, Gyeonggi-do (KR); Sung Ah Lee, Gyeonggi-do (KR); Mi Young Yoon, Chungcheongbuk-do (KR)

(73) Assignee: HK INNO.N CORPORATION, Seoul (KR)

( * ) Notice: Subject to any disclaimer, the term of this patent is extended or adjusted under 35 U.S.C. 154(b) by 0 days.

(21) Appl. No.: 16/629,082

(22) PCT Filed: Jul. 6, 2018

(86) PCT No.: PCT/KR2018/007693
§ 371 (c)(1),
(2) Date: Jan. 7, 2020

(87) PCT Pub. No.: WO2019/009661
PCT Pub. Date: Jan. 10, 2019

(65) Prior Publication Data
US 2020/0146974 A1    May 14, 2020

(30) Foreign Application Priority Data
Jul. 7, 2017   (KR) .................. 10-2017-0086696

(51) Int. Cl.
*A61K 9/00*       (2006.01)
*A61K 9/19*       (2006.01)
*A61K 31/4184*    (2006.01)
*A61K 47/26*      (2006.01)

(52) U.S. Cl.
CPC ............. *A61K 9/0019* (2013.01); *A61K 9/19* (2013.01); *A61K 31/4184* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 2,836,541 A | 5/1958 | Lager et al. | |
| 8,541,360 B2 * | 9/2013 | Brown ................ | A61K 9/0019 514/1.1 |
| 2005/0255161 A1 * | 11/2005 | Buyuktimkin ......... | A61K 47/10 424/486 |
| 2007/0142448 A1 | 6/2007 | Hanazawa et al. | |

FOREIGN PATENT DOCUMENTS

| | | |
|---|---|---|
| CN | 106377497 | 2/2017 |
| EP | 2 409 699 | 4/2014 |
| KR | 10-2014-0053952 | 5/2014 |
| KR | 10-2015-0024301 | 3/2015 |
| WO | 99/24073 | 5/1999 |
| WO | 2016/200148 | 12/2016 |

OTHER PUBLICATIONS

International Search Report (ISR) dated Nov. 13, 2018 in International (PCT) Application No. PCT/KR2018/007693.
Written Opinion dated Nov. 13, 2018 in International (PCT) Application No. PCT/KR2018/007693.

* cited by examiner

*Primary Examiner* — Brian J Davis
(74) *Attorney, Agent, or Firm* — Wenderoth, Lind & Ponack, L.L.P.

(57) ABSTRACT

The present disclosure relates to a composition for injection, which comprises a pharmaceutically acceptable salt of a compound represented by Formula 1 and one or more selected from mannitol, trehalose, lactose and glucose as a stabilizing agent, having improved stability.

15 Claims, 1 Drawing Sheet

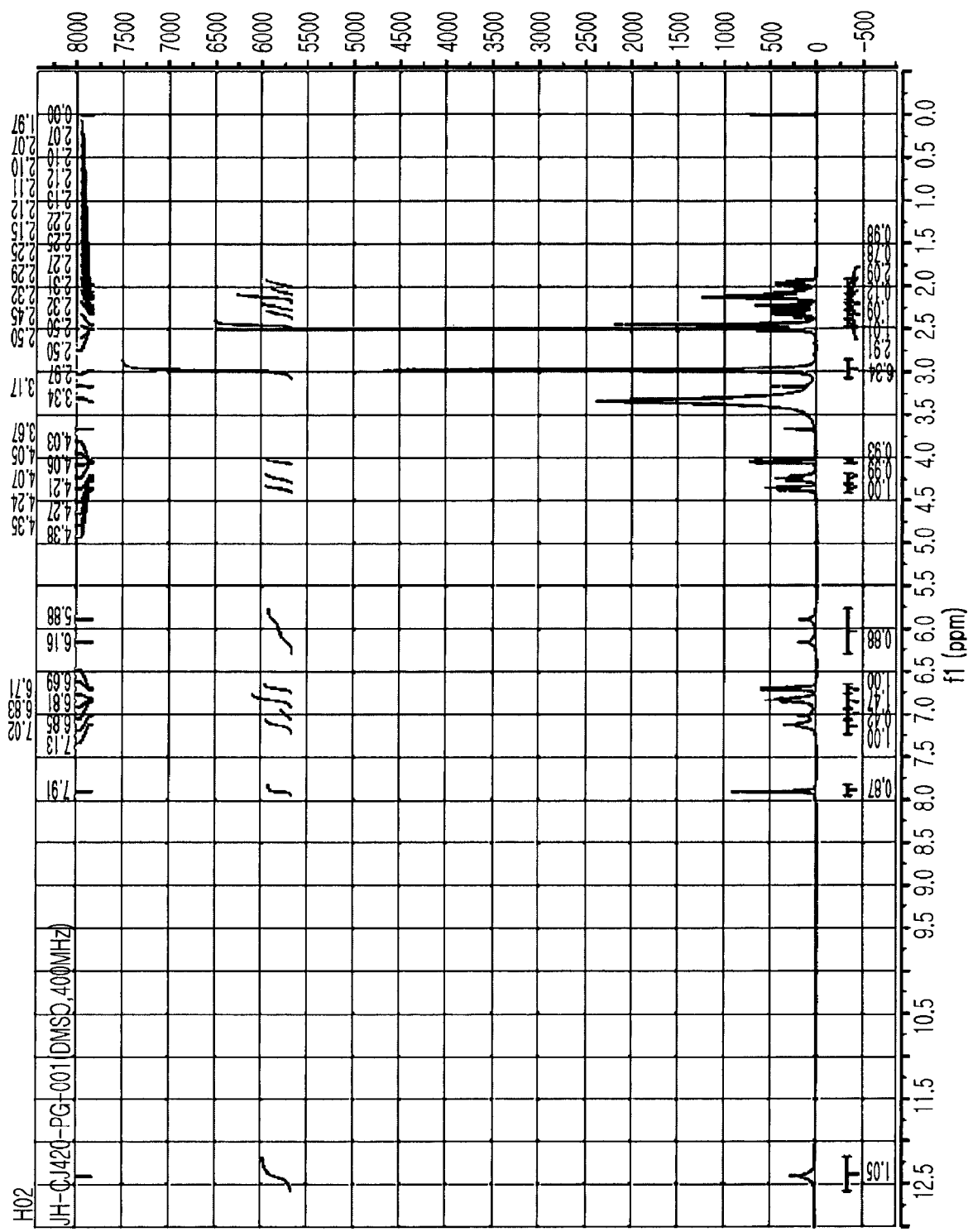

COMPOSITION FOR INJECTION

TECHNICAL FIELD

The present disclosure relates to a composition for injection comprising (S)-4((5,7-difluorochroman-4-yl)oxy)-N,N-2-trimethyl-1H-benzo[d]imidazole-6-carboxamide or a pharmaceutically acceptable salt thereof, and a method for preparing the same.

BACKGROUND ART (S)-4-((5,7-difluorochroman-4-yl)oxy)-N,N-2-trimethyl-1H-benzo[d]imidazole-6-carboxamide represented by a following Formula 1 is a pharmaceutically active component having a molecular weight of 387.39:

[Formula 1]

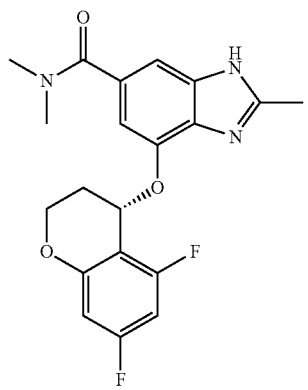

The compound is a pharmaceutical raw material, which has a use for preventing and treating diseases mediated by an acid pump antagonistic activity, including (but not limited to) gastrointestinal diseases, for example, a gastroesophageal disease, a gastroesophageal reflux disease, a peptic ulcer, a gastric ulcer, a duodenal ulcer, an ulcer induced by NSAID, a gastritis, a *Helicobacter pylori* infection, a dyspepsia, a functional dyspepsia, a Zollinger-Ellison syndrome, a nonerosive reflux disease (NERD), a visceral referred pain, a purosis, a nausea, an esophagitis, a dysphagia, a salivation, an airway lesion or an asthma.

However, the compound has a very low water solubility (0.02 mg/ml, pH 6.8), which increases (0.7 mg/ml, pH 3.0) under acid conditions, but not enough to have a significant effect. It is water insoluble and has a very low solubility, in particular, under neutral or higher pH environments, so it has a much difficulty in being formulated into preparations through its dissolution and stabilization in aqueous solutions. Also, its degradation products are increased under acid conditions, thus leading to poor stability and causing a restriction on selection of salts. Furthermore, in case of using solubilizers such as surfactants, etc., to improve the solubility, it requires an excessive amount of excipients, thus causing difficulty.

An excessive amount of solubilizers and organic solvents are required to develop drugs generally having a very low water solubility, including the compound represented by Formula 1 above, into compositions for injection. However, in case of pharmaceutical compositions containing solubilizers and organic solvents in large amounts, there is a problem in that hypersensitivity may occur upon administering a high dose of such components.

For example, doxetaxel, a well-known poorly water-soluble drug, is solubilized by using a highly viscous polysorbate. In this case, a problem occurs during its preparation because it is difficult to perform a 0.22 um filtration process, which is essential for preparing a formulation for injection. Furthermore, there is also a problem in that hypersensitivity reactions may occur due to a high dose of polysorbate used.

International Patent No. WO99/24073 discloses that a water solubility of doxetaxel was increased by means of a certain cyclodextrin. Said patent comprises a process of dissolving doxetaxel in a small amount of ethanol, adding acetyl gamma cyclodextrin (Ac-gamma-CD) or hydroxypropyl beta cyclodextrin (HP-beta-CD) therein, and dissolving a resultant mixture solution in an acqueous solvent. Also, it discloses a method for eliminating ethanol from the resultant solution above and freeze-drying resultant residues to prepare a freeze-dried composition. According to the patent above, however, there are disadvantages in that a very large amount of cyclodextrin is used to solubilize doxetaxel, thus leading to a large volume of freeze-dried products, a very low commercial productivity and a very high chance that the ethanol used in dissolving doxetaxel will remain.

Also, European Patent No. 2,409,699 describes a composition comprising hydroxypropyl-beta-cyclodextrin (HP-beta-CD) and glycine in order to stabilize voriconazole, which is a poorly water-soluble drug, but it still has an insufficient effect of maintaining stability under long-term accelerated or stress conditions.

In other words, in case of most of drugs having a low water solubility as mentioned above, it is very difficult to develop them into a preparation having such a high solubility as to be usable as an injection while having an excellent stability.

Thus, there is a demand for studying a formulation of the compound, which does not use a solubilizer such as ethanol or polysorbate likely to have a harmful effect as an injection, while having an excellent stability and securing a solubility enough to be used as an injection.

Accordingly, with regard to the compound represented by Formula 1, the present inventors have tried to develop a thermodynamically very stable injectable preparation while at the same time having an excellent water solubility and stability, thereby completing a composition for injection comprising the compound represented by Formula 1.

PRIOR ART REFERENCES

Patent Documents

International Patent No. WO99/24073
European Patent No. 2,409,699

DISCLOSURE OF INVENTION

Technical Problem

The objective of the present disclosure is to provide a composition for injection comprising a pharmaceutically acceptable salt of a compound represented by a following Formula 1 and one or more selected from mannitol, trehalose, lactose and glucose as a stabilizing agent, as well as a method for preparing the same:

[Formula 1]

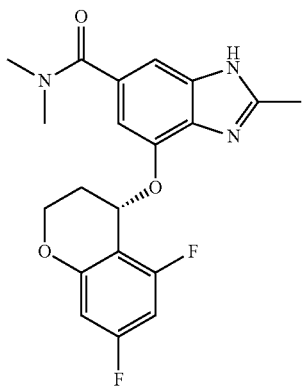

Specifically, a salt of the compound represented by Formula 1 may be a pidolate salt represented by a Formula 2 below:

[Formula 2]

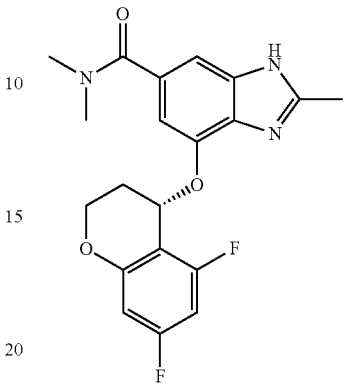 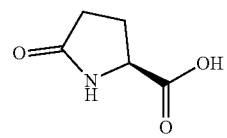

Solution to Problem

As a means of solving the above problem, the present disclosure provides a composition for injection comprising a pharmaceutically acceptable salt of a compound represented by Formula 1 and one or more selected from mannitol, trehalose, lactose and glucose as a stabilizing agent.

In the present disclosure, the compound represented by Formula 1 is a novel material for preventing and treating gastrointestinal diseases and bleeding related to the same according to a pharmacological mechanism of a potassium competitive acid blocker (P-CAB). The compound represented by Formula 1 is non-aqueous or poorly water-soluble in neutral to alkaline environments, and thus it is difficult to be developed into injections and also has a problem in that its chemical structural stability is extremely poor in acid environments in which a solubility comparatively increases, thus causing an increase in degradation products. To formulate the compound represented by Formula 1 into a composition for injection, it is necessary to succeed in dissolving the compound represented by Formula 1, while securing the stability of the resultant composition at the same time.

The present inventors have made an attempt at formulating various preparations in order to develop a composition for injection comprising a pharmaceutically acceptable salt of the compound represented by Formula 1, which is a poorly water-soluble drug, and thus have found that the composition for injection can achieve its complete dissolution and degradation stability as long as it comprises one or more selected from mannitol, trehalose, lactose and glucose as a stabilizing agent. Also, its preparational efficiency could be enhanced by simplifying a preparation process through an improved solubility.

In the present disclosure, a pharmaceutically acceptable salt of the compound represented by Formula 1 comprises an acid-addition salt. The acid-addition salt is, for example, acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hybenzate, hydrochloride/chloride, hydrobromide/bromide, hydroiodide/iodide, isethionate, lactate, malate, maleate, malonate, mesylate, methylsulphate, naphthylate, 2-napsylate, nicontinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, xinofoate, pidolate salts.

The composition for injection according to the present disclosure may comprise one or more selected from mannitol, trehalose, lactose and glucose as a stabilizing agent. They may be an anhydrous or a hydrated form. By comprising the stabilizing agent, it can have an excellent solubility while minimizing the production of impurities from the pharmaceutically acceptable salt of the compound represented by Formula 1.

The composition of the present disclosure is prepared prior to a process of freeze-drying a solution and comprises the pharmaceutically acceptable salt of the compound represented by Formula 1 and one or more selected from mannitol, trehalose, lactose and glucose. In the present disclosure, it may give an aid to process settings by figuring out a storage stability before freeze-drying the solution.

Also, the composition of the present disclosure comprises, for example, a solution prepared from freeze-dried powder or cake, which is reconstituted by saline solution or other pharmaceutically acceptable diluents. The composition of the present disclosure further comprises a solution obtained in such a way that the reconstituted solution is diluted with a pharmaceutically acceptable diluent.

A composition for injection according to the present disclosure may comprise a pharmaceutically acceptable salt of the compound represented by Formula 1 and one or more selected from mannitol, trehalose, lactose and glucose as a stabilizing agent. A content of said stabilizing agent is 0.5-3.0 parts by weight, more particularly 0.7-2.0 parts by weight with respect to 1 part by weight of the pharmaceutically acceptable salt of the compound represented by Formula 1. In case of using more than 3.0 parts by weight of the stabilizing agent, there is a disadvantage in that a viscosity of its solution increases too much, and thus its filtration becomes impossible after dissolution and its freeze drying takes too much time.

Specifically, the composition for injection according to the present disclosure is in the form of liquid or dried powder. The dry powder for injection may be administered to patients in such a way that it is reconstituted by WFI, physiological salt solution, glucose solution, amino acid solution, etc.

The drying may be performed by means of a conventional drying method, for example, freeze drying, spray drying or fluid bed drying, preferably freeze drying.

In one embodiment of the present disclosure, in case of the composition for injection comprising the pharmaceutically acceptable salt of the compound represented by Formula 1 and the stabilizing agent in an amount of 0.7 to 2.0 parts by weight with respect to 1 part by weight of the compound, it was identified that there was no change in its properties and no drastic increase in its total impurities and individual impurities under stress conditions, and a stability of the composition could be maintained.

According to the present disclosure, pH of the composition for injection may be present in a range of 3.0 to 5.0, particularly in a range of 3.5 to 4.5. If pH of the composition for injection is 3.0 or less, degradation products of active components increase. If pH thereof is 5.0 or more, there is a problem in that a content of active components in the composition decreases. The pH may be adjusted by adding of a pH-controlling agent in the composition, etc., wherein conventional pH-controlling agents, e.g., hydrochloric acid, sodium hydroxide or the like, used for regulating pH of compositions upon preparing the compositions for injection, may be used therein without a limitation.

In one embodiment of the present disclosure, as a result of analyzing the stability of compositions for injection with different pHs comprising a pharmaceutically acceptable salt of the compound represented by Formula 1 and one or more selected from mannitol, trehalose, lactose and glucose as a constitution of the composition for injection, it was identified that the composition having a pH of 3.0 to 5.0 showed no change in its properties of the composition, produced a less amount of total impurities, and stably maintained a content of the compound of Formula 2 during a period of storage, while the composition having pH 2.0 or less showed an increase in impurities and a decrease in a content of the compound of Formula 2 during the same period.

Likewise, the composition for injection of the present disclosure has advantages that it can secure a solubility necessary for constituting the composition for injection and can be stably stored for a long period of time in such a way that it comprises one or more selected from mannitol, trehalose, lactose and glucose and its pH is adjusted to be within a range of 3.0 to 5.0.

An amount of active components contained in the composition for injection of the present disclosure varies depending on a condition of a target patient for administration, a degree of targeted treatment, etc. Preferably, the composition of the present disclosure may be comprised at a concentration of 1 to 200 mg/mL based on the compound of Formula 1, preferably at a concentration of 1 to 50 mg/mL. If the active components are comprised at a low concentration of 1 mg/mL or less, a large dose of injectible solution is required to exhibit a sufficient therapeutic effect, thus causing a difficulty in being administered to an affected area of a patient. If they are comprised at a high concentration of 200 mg/mL or more, it is difficult to satisfy the composition that dissolves even the stabilizing agent, and precipitation may take place or impurities may occur during resuspension or dissolution.

When preparing the composition for injection according to the present disclosure, WFI may be used to do so. An injection containing the pharmaceutically acceptable salt of the compound of Formula 1 according to the present disclosure do not have to comprise other additives than a stabilizing agent and a pH-controlling agent, but may further optionally comprise, without a limitation, an isotonic agent, a buffer solution, an osmotic agent, etc., which are conventionally used in the art.

Advantageous Effects of Invention

A composition for injection according to the present disclosure can be usefully used as an injection because it can completely dissolve active components, shows a very low generation rate of impurities, and can be stored for a long period of time.

BRIEF DESCRIPTION OF DRAWINGS

The FIGURE shows 1H-NMR result of a compound represented by formula 2 prepared according to one embodiment of the present disclosure.

MODE FOR THE INVENTION

Hereinafter, the present disclosure will be described in detail through preferred Examples for better understanding of the present disclosure. However, the following Examples are provided only for the purpose of illustrating the present disclosure, and thus the present disclosure is not limited thereto.

Preparing Example: Preparing of a Pidolate Salt Represented by Formula 2

100 g of a crystalline compound of Formula 1 and L-pyroglutamic acid (34.98 g, 1.05 eq.) were completely dissolved at 25° C. in 1000 ml of methanol, after which such prepared mixture was concentrated while being stirred under reduced pressure at 50° C. until solids were precipitated. A co-solvent, which was a mixture of aceton/ethyl acetate=1/4 (500 ml), was added into the above resultant concentrate at 25° C., and then they were violently stirred for 30 minutes. Then, the solids were filtered out under reduced pressure, and washed with 100 ml of ethyl acetate, after which the resultant solids were dried under vacuum at 40° C. for 16 hours, to obtain 113.8 g (yield 85.4%) of amorphous compound represented by Formula 2 in white powder (the FIGURE).

Examples 1 to 9: Identification of the Properties of the Compound for Injection and the Amount of Total Impurities Therein, when Mannitol Added The compound (1000 mg) represented by Formula 2 was dissolved in WFI (50 mL) to prepare a bulk solution. An aliquot (5 mL) of the solution containing about 100 mg of the principal ingredient (the compound represented by Formula 2) was dissolved in each of 20 mL vials containing 100 mg of mannitol, after which 1.0 N HCl was added into each of the above prepared mixtures, such that pH was adjusted to 2.0, 2.5, 3.0 and 4.0 respectively. An aliquot of the bulk solution was put into an empty 20 mL sample vial, without pH adjustment, and all the prepared solutions were freeze-dried. Every freeze drying was performed by using a freeze dryer. After freeze drying is completed, the freeze-dried samples were left in a chamber with 60° C./relative humidity of 80% for 4 weeks. Then, the samples were analyzed by means of an HPLC, their stabilities were evaluated based on the amount of total impurities produced during storage, and analysis conditions for measuring a content of the impurities were such as those shown in the following:

Column: A column filled with octadecyl silica gel for liquid chromatography
Column temperature: Constant temperature around 30° C.
Detector: UV absorptiometer (measured wavelength: 220 nm)
Flow rate: 0.8 mL/min
Mobile phase gradient conditions

| Time (Minute) | Mobile Phase | |
| --- | --- | --- |
| | Mobile Phase A (%) | Acetonitrile (%) |
| 0 | 88 | 12 |
| 2 | 88 | 12 |
| 3 | 70 | 30 |
| 15 | 70 | 30 |
| 16 | 20 | 80 |
| 18 | 10 | 90 |
| 20 | 10 | 90 |
| 20.1 | 88 | 12 |
| 25 | 88 | 12 |

The results were indicated in a peak area (%) for total impurities relative to total area of peaks, as shown in a following Table 1.

TABLE 1

| | | Total Impurities (%) | Property after reconstitution |
| --- | --- | --- | --- |
| Example 1 | Freeze drying only Formula 2 (pH 4.0) | 0.42 | Transparent |
| Example 2 | Formula 2 + Mannitol (pH 4.0) | 0.17 | Transparent |
| Example 3 | Formula 2 + Mannitol (pH 3.0) | 0.23 | Transparent |
| Example 4 | Formula 2 + Mannitol (pH 2.5) | 0.30 | Transparent |
| Example 5 | Formula 2 + Mannitol (pH 2.0) | 0.37 | Transparent |

In Example 1, in which only the principal ingredient was freeze-dried, it was demonstrated that an amount (%) of total impurities accounted for 0.42%, thus showing a quite poor stability. On the other hand, in Example 2 according to the present disclosure, an amount of total impurities accounted for 0.17%, thus showing a great increase in stability. Meanwhile, observation a change in total impurities depending on pH showed that an amount of impurities tended to increase at a lower pH, i.e., a low amount of total impurities occurring between pH 3.0 and 5.0.

Also, an experiment was performed with different pH conditions by means of the same method as in Examples 1 to 5 above.

To prepare a composition for injection, the compound (1000 mg) represented by Formula 2 was dissolved in WFI (50 mL) to prepare a bulk solution. According to the same method for preparing the solution as in Example 1, 1.0N NaOH was added into each of solutions containing the principal ingredient (about 100 mg) and 100 mg of mannitol, after which pHs were adjusted to about pH 4.5, 5.0, 5.5 and 6.0. And then, all the samples were dried by using a Christi Epsilon 2-10D freeze dryer. The freeze-dried samples were left in a chamber with 60° C./relative humidity of 80% for 4 weeks, after which, upon the completion of storage, their impurities were analyzed with an HPLC, such that results thereof were indicated as shown in Table 2. After the completion of storage for 4 weeks, freeze-dried cakes were reconstituted at a concentration of 10 mg/mL by using physiological salt solution, after which the prepared solutions were stored at a room temperature.

TABLE 2

| | | Total Impurities (%) | Property after reconstitution |
| --- | --- | --- | --- |
| Example 6 | Formula 2 + Mannitol (pH 4.5) | 0.18 | Transparent |
| Example 7 | Formula 2 + Mannitol (pH 5.0) | 0.16 | Transparent |
| Example 8 | Formula 2 + Mannitol (pH 5.5) | 0.17 | Opaque |
| Example 9 | Formula 2 + Mannitol (pH 6.0) | 0.15 | Opaque |

As a result of identifying properties alter such reconstitution, it was demonstrated that the samples after the reconstitution had a low amount of total impurities at pH 5.0 or less and exhibited transparent properties.

Examples 10 to 11: Identification of the Amount of Total Impurities of the Composition for Injection, Depending on Types and Amounts of Stabilizing Agents The compound (1000 mg) represented by Formula 2 was dissolved in WFI (50 mL) to prepare a solution. An aliquot (5 mL) of the solution containing about 100 mg of the principal ingredient was dissolved in each of vials containing 100 mg of mannitol or 100 mg of trehalose, after which all the prepared solutions were dried by means of a freeze-drying method without pH adjustment. After then, the prepared freeze-dried samples were left in a chamber with 60° C./relative humidity of 80% for 4 weeks. Then, the samples were analyzed by means of an HPLC, after which results thereof were summarized in a Table 3 to show results of key degradation products with regard to each cake.

TABLE 3

| | | Total Impurities (%) |
| --- | --- | --- |
| Example 10 | Principal ingredient + Mannitol 100 mg | 0.17 |
| Example 11 | Principal ingredient + Mannitol 100 mg | 0.05 |

As a result of Examples 10 and 11, it was demonstrated that there was a great improvement in the stability of the compound comprising the principal ingredient, and mannitol, trehalose, lactose or glucose.

However, in case of the composition for injection comprising 50 mg of mannitol or trehalose under the same conditions, an amount of total impurities was greatly increased because of a low content of a stabilizing agent. Also, in case of containing 300 mg or more of mannitol or trehalose, which amounts to a high weight, there were disadvantages that a volume became excessively large and it took a long time to prepare the composition by means of the freeze-drying method.

Examples 12 to 17: Identification of Properties of the Composition for Injection and a Content of Total Impurities The compound (1000 mg) represented by Formula 2 was dissolved in WFI (50 mL) to prepare a solution. An aliquot (5 mL) of the solution containing about 100 mg of the principal ingredient was dissolved in each of vials containing 100 mg of mannitol or 100 mg of trehalose, after which 1.0N HCl and 1.0N NaOH were added into each of the above prepared mixtures to adjust pH to 2.0, 4.0 and 6.0 respectively and freeze drying was performed. After then, the resultant freeze-dried samples were left in a chamber with 60° C./relative humidity of 80% for 4 weeks. After such storage, the samples were analyzed to figure out their total impurities and a trend of their properties after reconstitution.

TABLE 4

| | | pH | Total Impurities (%) | Property after reconstitution |
|---|---|---|---|---|
| Example 12 | Principal ingredient + Mannitol 100 mg | 2.0 | 0.37 | Transparent |
| Example 13 | Principal ingredient + Mannitol 100 mg | 4.0 | 0.17 | Transparent |
| Example 14 | Principal ingredient + Mannitol 100 mg | 6.0 | 0.18 | Opaque |
| Example 15 | Principal ingredient + Trehalose 100 mg | 2.0 | 0.21 | Transparent |
| Example 16 | Principal ingredient + Trehalose 100 mg | 4.0 | 0.05 | Transparent |
| Example 17 | Principal ingredient + Trehalose 100 mg | 6.0 | 0.05 | Opaque |

As shown in the Table 4, in case of compositions of Examples 13, 14, 16 and 17 according to the present disclosure, it could be seen that the amounts of total impurities remain constant when pH changes. However, in case of preparing a composition at pH 6.0, it was demonstrated that the composition was inappropriate due to its opaque properties after reconstitution. In case of Examples 12 and 15, it could be seen that an amount of impurities was increased due to influence of pH 2.0. Thus, in case of a preparation, which comprises mannitol, trehalose or both thereof and in which the composition has a pH ranging from 3.0 to 5.0, it could be seen that such preparation is a formulation which can maintain its cake appearance during storage as well as its solubility upon reconstitution and also can have an excellent stability with no change in content and little generation of impurities.

While specific portions of the present disclosure have been described in detail above, it is apparent to those skilled in the art that such detailed descriptions are set forth to illustrate exemplary embodiments only, but are not construed to limit the scope of the present disclosure. Thus, it will be understood that the substantial scope of the present disclosure is defined by the accompanying claims and equivalents thereto.

The invention claimed is:

1. An injectable composition comprising:
a pharmaceutically acceptable salt of a compound represented by the following Formula 1; and
at least one stabilizing agent selected from the group consisting of mannitol, trehalose, lactose and glucose:

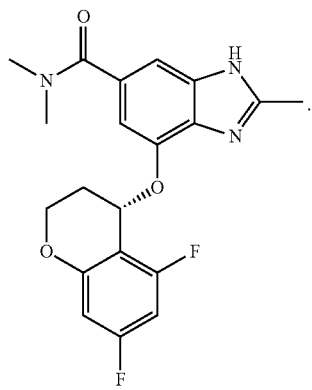

[Formula 1]

2. The injectable composition according to claim 1, wherein the pharmaceutically acceptable salt of the compound represented by Formula 1 is a compound represented by the following Formula 2:

[Formula 2]

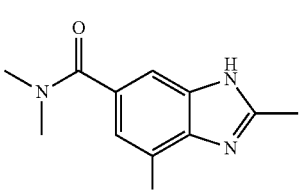
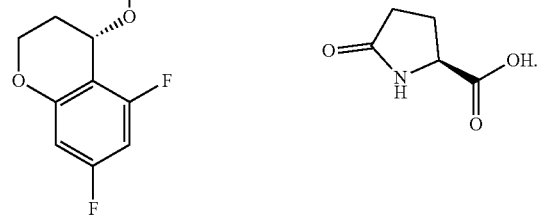

3. The injectable composition according to claim 1, wherein the stabilizing agent is mannitol or trehalose.

4. The injectable composition according to claim 1, wherein the stabilizing agent is present in an amount of 0.5 to 3.0 parts by weight with respect to 1 part by weight of the pharmaceutically acceptable salt of the compound represented by Formula 1.

5. The injectable composition according to claim 1, wherein the pH of the injectable composition ranges from 3.0 to 5.0.

6. The injectable composition according to claim 1, wherein the injectable composition is in the form of liquid or dried powder.

7. The injectable composition according to claim 1, wherein the injectable composition further comprises at least one ingredient selected from the group consisting of an isotonic agent, a buffer solution, an osmotic agent and a pH-controlling agent.

8. The injectable composition according to claim 2, wherein the stabilizing agent is mannitol or trehalose.

9. The injectable composition according to claim 2, wherein the stabilizing agent is present in an amount of 0.5 to 3.0 parts by weight with respect to 1 part by weight of the pharmaceutically acceptable salt of the compound represented by Formula 1.

10. The injectable composition according to claim 2, wherein the pH of the injectable composition ranges from 3.0 to 5.0.

11. The injectable composition according to claim 2, wherein the injectable composition is in the form of liquid or dried powder.

12. The injectable composition according to claim 2, wherein the injectable composition further comprises at least one ingredient selected from the group consisting of an isotonic agent, a buffer solution, an osmotic agent and a pH-controlling agent.

13. A method for preventing or treating a disease mediated by an acid pump antagonistic activity, the method comprising administering the injectable composition according to claim 1 to a patient.

14. The method according to claim 13, wherein the disease mediated by an acid pump antagonistic activity is at least one gastrointestinal disease selected from the group consisting of a gastroesophageal disease, a gastroesophageal reflux disease, a peptic ulcer, a gastric ulcer, a duodenal ulcer, an ulcer induced by NSAID, a gastritis, a *Helicobacter pylori* infection, a dyspepsia, a functional dyspepsia, a Zollinger-Ellison syndrome, a nonerosive reflux disease (NERD), a visceral referred pain, a purosis, a nausea, an esophagitis, a dysphagia, a salivation, an airway lesion and an asthma.

15. A method of administering the injectable composition according to claim 1, comprising administering the injectable composition to a patient.

* * * * *